United States Patent
Huang et al.

(10) Patent No.: US 9,823,159 B2
(45) Date of Patent: Nov. 21, 2017

(54) LOW CYCLE FATIGUE TESTING

(71) Applicant: DMAR ENGINEERING, INC., Houston, TX (US)

(72) Inventors: Zhiming Huang, Missouri City, TX (US); Dagang Zhang, Houston, TX (US)

(73) Assignee: DMAR Engineering, Inc., Houston, TX (US)

( * ) Notice: Subject to any disclaimer, the term of this patent is extended or adjusted under 35 U.S.C. 154(b) by 186 days.

(21) Appl. No.: 14/658,245

(22) Filed: Mar. 16, 2015

(65) Prior Publication Data

US 2016/0273997 A1 Sep. 22, 2016

(51) Int. Cl.
*G01M 3/28* (2006.01)
*G01N 3/36* (2006.01)
*G01N 3/20* (2006.01)

(52) U.S. Cl.
CPC ........ *G01M 3/2884* (2013.01); *G01M 3/2846* (2013.01); *G01N 3/20* (2013.01); *G01N 3/36* (2013.01); *G01N 2203/0023* (2013.01); *G01N 2203/0048* (2013.01); *G01N 2203/0073* (2013.01); *G01N 2203/0274* (2013.01)

(58) Field of Classification Search
CPC .. G01N 3/32; G01N 3/36; G01N 3/20; G01N 2203/0023; G01N 2203/0073; G01N 2203/0274; G01M 3/2884
USPC ........ 73/804, 808, 809, 810, 812, 813, 814, 73/815, 850, 849, 49.1
See application file for complete search history.

(56) References Cited

U.S. PATENT DOCUMENTS

| | | | | | |
|---|---|---|---|---|---|
| 3,845,657 A | * | 11/1974 | Hall | ........................ | G01M 3/40 138/104 |
| 4,063,453 A | * | 12/1977 | Gram | ........................ | G01N 3/10 100/214 |
| 4,428,187 A | * | 1/1984 | Bruce | ....................... | F16G 15/02 59/85 |
| 4,478,086 A | * | 10/1984 | Gram | ........................ | G01N 3/08 73/781 |
| 7,204,152 B2 | * | 4/2007 | Woodward | ................ | G01N 3/32 73/794 |
| 2011/0176125 A1 | * | 7/2011 | Smith | ................... | G01B 11/165 356/32 |
| 2013/0247680 A1 | * | 9/2013 | Ota | ........................... | G01N 3/12 73/788 |
| 2016/0131563 A1 | * | 5/2016 | Shafer | ....................... | G01N 3/36 73/37 |

* cited by examiner

*Primary Examiner* — Laura Martin
*Assistant Examiner* — Suman K Nath
(74) *Attorney, Agent, or Firm* — Liaoteng Wang

(57) ABSTRACT

Apparatus and methods related to low cycle fatigue testing are described. For example, some embodiments may contain a control box, two fitting connections, a pressure gauge, a plurality of clamps, a plurality of hydraulic cylinders, a plurality of control cables, and a strain gauge, for testing the low cycle fatigue properties of a testing specimen, for example, a steel tube umbilical.

20 Claims, 2 Drawing Sheets

LOW CYCLE FATIGUE TESTING

FIELD OF PRESENT DISCLOSURE

This present disclosure relates to low cycle fatigue testing.

BACKGROUND INFORMATION

Low cycle fatigue testing can be used to evaluate the fatigue performance of small diameter tube butt welds at high stress range, high strain deformation, and low cycle numbers. It is commonly used for testing the fatigue properties of tubing welds present in the subsea control system. For example, during steel tube umbilical fabrication, the umbilical may experience large deformation when it passes through a radius controller, or stored on a reel. Such large deformation can be beyond the steel yield range, when the steel tube will go beyond the elastic deformation region, and experience certain degree of plastic deformation, which will not reverse, and thereby cause permanent elongation in the tube, and generate significant fatigue damage to the tube, which is called low cycle fatigue. Welds and connection joints are usually the weakest point for low cycle fatigue. During the test, the tube-shaped testing specimen is bent to the desired radius, and the smaller the radius, the higher the strain and stress, which sometimes can be beyond the yield stress. Next the tube-shaped testing specimen is straightened out to complete one cycle. After repeating this bending-straightening process for a certain number of cycles, the specimen will experience fatigue crack and fail eventually. Conventional testing method uses a pre-fabricated disc or cylinder, each with a defined radius, to bend the tube into the desired radius, then straighten the bent tube through a tube straightener or tension pull, which can be time-consuming, and sometimes produces biased testing results by introducing excessive tension loads. During steel tube umbilical fabrication, the steel tube usually bends into one direction first, and then bends into the opposite direction in the following cycle, which is not reflected in the conventional testing method. Apparatus and methods have been proposed for performing low cycle fatigue testing, which, among other applications, can be used for testing the fatigue performance of the umbilical (or steel tube bundle), which can experience low cycle fatigue during the fabrication process.

DETAILED DESCRIPTION

Figure 1:
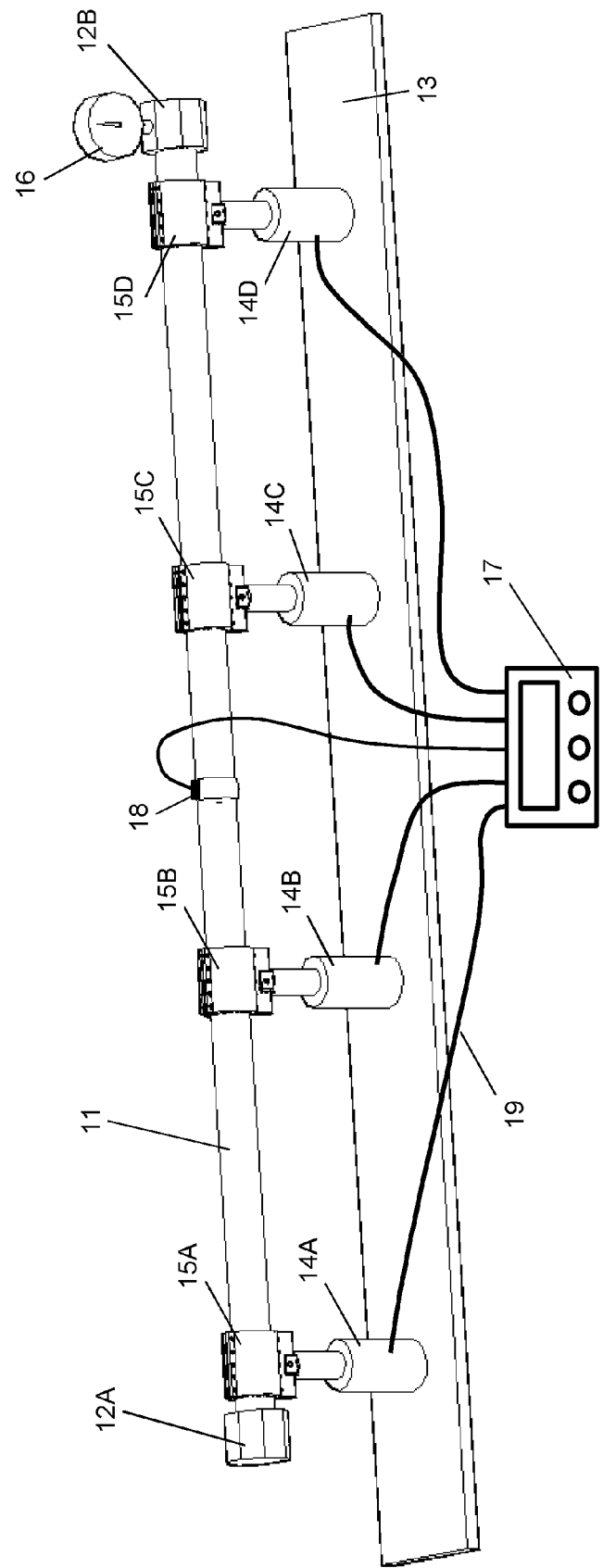
FIG. 1 is a schematic diagram showing an embodiment of the apparatus and methods for low cycle fatigue testing.
Figure 2:
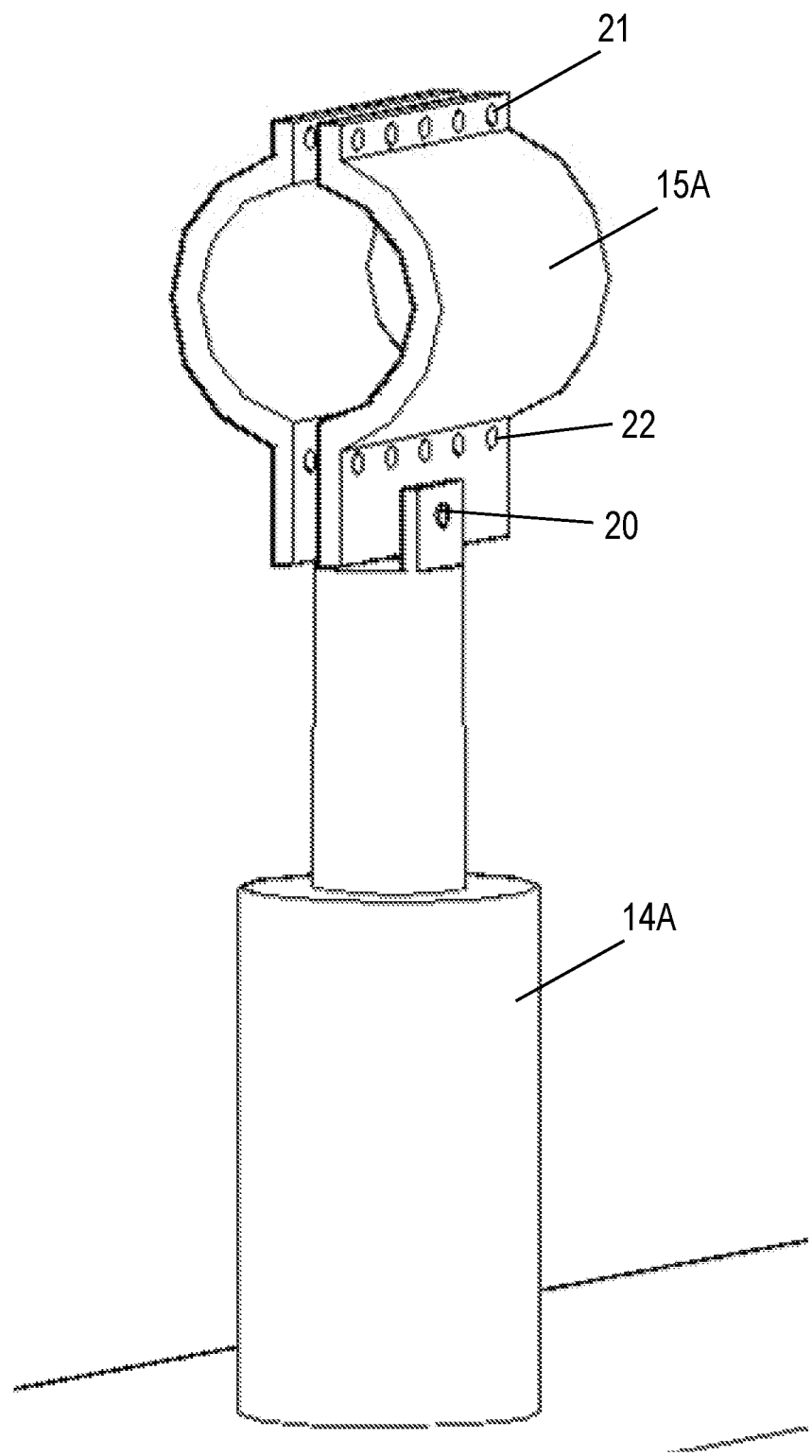
FIG. 2 is a schematic diagram showing an embodiment of a tube clamp connected to a hydraulic cylinder for conducting the low cycle fatigue testing.

This document discloses apparatus and methods related to low cycle fatigue testing. FIG. 1 shows an implementation of the apparatus and methods for low cycle fatigue testing. The testing apparatus can comprise two fitting connections 12A and 12B (which can be mounted on the two ends of a tube-shaped testing specimen 11, keeping the testing tube watertight), a plurality of hydraulic cylinders 14A, 14B, 14C, and 14D, which can be arranged on a testing platform 13, a plurality of clamps 15A, 15B, 15C, and 15D, a pressure gauge 16 for monitoring the internal pressure of the testing tube, a control box 17, a strain gauge 18, and a plurality of control cables 19. The clamp 15 can be positioned along the testing specimen 11, and may or may not be evenly distributed along the length of the testing specimen 11, but may be positioned flexibly based on the testing requirements. As shown in FIG. 2, the hydraulic cylinders 14 can connect to the clamps 15 through a pivot pin 20. The clamps 15 can consist of two half shells 15A that can be assembled together through bolts 21 and 22.

In some implementations, the testing specimen 11 has the butt weld located near its center region, and a strain gauge 18 is attached on the outer surface on or near the weld or joint connection area of the testing specimen 11. The strain gauge 18 is connected to the control box 17 through a signal cable 19. Control box 17 receives strain gauge reading during the low cycle fatigue test continuously. In some implementations, the control box can be a computer with suitable peripherals capable of receiving signals from the strain gauge 18, analyzing the signals to find out the bending status of the testing specimen and sending signals to hydraulic cylinders 14 to adjust the cylinder extension and retraction pattern, to control the testing automatically based on predefined testing purposes. In some implementations, the control box 17 allows for loading of new programs for new tests, and has a screen for displaying all controlled parameters useful for the low cycle fatigue testing, and an input device such as a keyboard for machine-human interaction.

In some implementations, the hydraulic cylinders 14 are connected to the control box 17 through control cables 19. The control box 17 sends signals to the hydraulic cylinders 14 to extend or retract the piston as needed during the low cycle fatigue test.

In some implementations, the tube-shaped testing specimen 11 may have a length from 0.5 meter to 5 meters.

In some implementations, the testing specimen 11 may be tensioned through end cap effect from internal pressure, or through external hydraulic cylinders 14, or through external clump weight, or through the clamps 15 located near its two ends.

In some implementations, the low cycle fatigue test can be carried out as follows: (i) fill up the testing tube 11 with water or other testing fluid, and pressurize the testing tube 11 to a predefined level; (ii) attach all clamps 15 and connect all components; (ii) set the minimum curvature and maximum curvature range in the control box 17; (iii) start the low cycle fatigue test, whereby the control box 17 will instruct the hydraulic cylinders 14 to bend the testing tube 11 until the maximum curvature is reached at the strain gauge 18, and then reverse to the minimum curvature; and (iv) repeat the same process until the pressure gauge 18 records a tube leakage failure, when the bending cycle number is recorded. A series of tests can be performed, after which data analysis is carried out to determine the fatigue curve parameters of the testing specimen 11.

OTHER EMBODIMENTS

Various other adaptations and combinations of features of the embodiments and implementations disclosed are within the scope of the present disclosure. It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An apparatus for low cycle fatigue testing on a testing specimen, comprising:
   a testing platform;
   a plurality of hydraulic cylinders arranged along a length of the testing platform, the hydraulic cylinders extending and retracting along parallel axes of the plurality of hydraulic cylinders that are displaced from each other;
   a plurality of clamps positioned along a length of the testing specimen, each clamp being connected to a respective one of the plurality of hydraulic cylinders;
   a strain gauge attached to an outer surface of the testing specimen;
   a plurality of control cables and a signal cable; and
   a control box connected by the plurality of control cables to the plurality of hydraulic cylinders and by the signal cable to the strain gauge, wherein the control box performs the low cycle fatigue testing by analyzing data from the strain gauge.

2. The apparatus according to claim 1, further comprising two fitting connections.

3. The apparatus according to claim 2, wherein the two fitting connections are connected to a tube-shaped testing specimen at its two ends.

4. The apparatus according to claim 2, further comprising a pressure gauge.

5. The apparatus according to claim 4, wherein the pressure gauge is connected to one of the two fitting connections.

6. The apparatus according to claim 1, herein the clamps are adjustably positioned along a tube-shaped testing specimen.

7. The apparatus according to claim 1, wherein each clamp comprises two half shells that are assembled together through bolts to hold the testing specimen in place.

8. The apparatus according to claim 1, wherein the clamps are connected to the plurality of hydraulic cylinders through pivot pins.

9. The apparatus according to claim 1, wherein the strain gauge is attached to the testing specimen on or near a weld or joint connection area of the testing specimen.

10. The apparatus according to claim 1, wherein the control box is connected to the strain gauge to receive a plurality of strain values.

11. The apparatus according to claim 10, wherein the control box is receiving the strain values from the strain gauge and displaying it in real time.

12. The apparatus according to claim 1, wherein the control box instructs the hydraulic cylinders to extend or retract in a pattern.

13. The apparatus according to claim 1, wherein the testing specimen is tube-shaped and has a length of 0.5 meter to 5 meters.

14. The apparatus according to claim 1, wherein the testing specimen is tensioned during the low cycle fatigue testing.

15. The apparatus according to claim 14, wherein the tension is achieved through at least one of an internal pressure, a clump weight, an external hydraulic cylinder, or two clamps at the two ends of the testing specimen.

16. A method for low cycle fatigue testing on a testing specimen, comprising:
    attaching a strain gauge to an area on a surface of the testing specimen;
    connecting the strain gauge to a control box via a signal cable;
    attaching a plurality of clamps along a length of the testing specimen;
    attaching the clamps to a plurality of hydraulic cylinders, the plurality of hydraulic cylinders being oriented to extend and retract along parallel axes of the plurality of hydraulic cylinders that are displaced from each other;
    connecting the plurality of hydraulic cylinders to the control box via a plurality of control cables; and
    operating the control box to (1) send signals to the plurality of hydraulic cylinders to bend the testing specimen and (2) receive strain gauge reading from the strain gauge wherein the control box performs the low cycle fatigue testing by analyzing data from the strain gauge.

17. The method according to claim 16, wherein the strain gauge is placed on or near a weld or joint connection area of the testing specimen.

18. The method according to claim 16, wherein the testing specimen is a tube that is filled with water or other testing fluid at a desired pressure that is continuously monitored by a pressure gauge.

19. The method according to claim 16, wherein the control box is a computer with suitable peripherals receiving data from the strain gauge, analyzing the data to determine a bend of the testing specimen, and sending the signals to the plurality of hydraulic cylinders to adjust corresponding cylinder extension and retraction pattern to control the low cycle fatigue testing based on predefined testing purposes.

20. The method according to claim 18, wherein a minimum curvature and a maximum curvature are set in the control box, and, in a bending process, the control box instructs the hydraulic cylinders to bend the testing specimen until the maximum curvature is reached at the strain gauge and then reverse the bending to the minimum curvature, and the control box repeats the bending process until the pressure gauge indicates a tube leakage failure, at which time the control box records the corresponding bending cycle number.

* * * * *